(12) United States Patent
Jaramaz et al.

(10) Patent No.: US 11,896,237 B2
(45) Date of Patent: Feb. 13, 2024

(54) IMPLANT CUTTING BLOCK PIN PLACEMENT

(71) Applicant: Smith & Nephew, Inc., Memphis, TN (US)

(72) Inventors: Branislav Jaramaz, Pittsburgh, PA (US); Constantinos Nikou, Monroeville, PA (US)

(73) Assignee: Smith & Nephew, Inc., Memphis, TN (US)

(*) Notice: Subject to any disclaimer, the term of this patent is extended or adjusted under 35 U.S.C. 154(b) by 190 days.

(21) Appl. No.: 17/523,238

(22) Filed: Nov. 10, 2021

(65) Prior Publication Data
US 2022/0061856 A1 Mar. 3, 2022

Related U.S. Application Data

(63) Continuation of application No. 16/742,290, filed on Jan. 14, 2020, now Pat. No. 11,197,679, which is a continuation of application No. 16/066,939, filed as application No. PCT/US2017/063901 on Nov. 30, 2017, now Pat. No. 11,051,830.

(60) Provisional application No. 62/428,427, filed on Nov. 30, 2016.

(51) Int. Cl.
*A61B 17/15* (2006.01)
*A61B 34/20* (2016.01)
*A61B 17/16* (2006.01)
*A61B 34/10* (2016.01)
*A61B 17/17* (2006.01)

(52) U.S. Cl.
CPC ........ *A61B 17/157* (2013.01); *A61B 17/1675* (2013.01); *A61B 34/10* (2016.02); *A61B 34/20* (2016.02); *A61B 17/1703* (2013.01); *A61B 17/1764* (2013.01); *A61B 2034/108* (2016.02); *A61B 2034/2055* (2016.02); *A61B 2034/2057* (2016.02)

(58) Field of Classification Search
CPC .......................... A61B 17/157; A61B 17/1675
See application file for complete search history.

(56) References Cited

U.S. PATENT DOCUMENTS

2015/0245879 A1* 9/2015 Nikou .................... A61B 34/10
606/88

* cited by examiner

*Primary Examiner* — Sameh R Boles
(74) *Attorney, Agent, or Firm* — DLA Piper LLP

(57) ABSTRACT

A system, method, and device for drilling holes (420, 422) in a target bone (414) are described. For example, the system includes a cutting tool (330), a navigation system (310) configured to track a position of the cutting tool, and a computer-assisted surgical (CAS) system (340) operably connected to the cutting tool and the navigation system. The CAS system can be configured to determine an implant component (100) to be implanted on the target bone (414), determine a cutting block position for preparing the target bone to receive the implant component, determine a plurality of pin locations (420, 422) for securing the cutting block (416) based upon the determined cutting block position, and selectively provide instructions to the cutting tool to cut a hole when the cutting tool is in a position adjacent to at least one of the determined plurality of pin locations.

14 Claims, 9 Drawing Sheets

IMPLANT CUTTING BLOCK PIN PLACEMENT

CLAIM OF PRIORITY

This application is a continuation of U.S. patent application Ser. No. 16/742,290, titled "Implant Cutting Block Pin Placement," filed Jan. 14, 2020, which is a continuation of U.S. patent application Ser. No. 16/066,939, titled "Implant Cutting Block Pin Placement," filed Jun. 28, 2018, now U.S. Pat. No. 11,051,830, which is a U.S. national stage filing under 35 U.S.C. § 371 of International PCT Application No. PCT/US2017/063901, filed Nov. 30, 2017, which claims the benefit of priority to U.S. Provisional Patent Application No. 62/428,427, titled "Implant Cutting Block Pin Placement," filed on Nov. 30, 2016, each of which is incorporated herein by reference in its entirety.

TECHNICAL FIELD

The present disclosure relates generally to apparatus, methods, and systems for computer-aided orthopedic surgery. More specifically, the present disclosure relates to using computer-aided drilling device alignment to control cutting block pin-hole placement to make implant surgery more efficient.

BACKGROUND

The use of computers, robotics, and imaging to aid orthopedic surgery is well known in the art. There has been a great deal of study and development of computer-aided navigation and robotic systems used to guide surgical procedures. For example, a precision freehand sculptor (PFS) employs a robotic surgery system to assist the surgeon in accurately cutting a bone into a desired shape. In procedures such as total hip replacement, computer-aided surgery techniques have been used to improve the accuracy, reliability of the surgery. Orthopedic surgery guided by images has also been found useful in preplanning and guiding the correct anatomical position of displaced bone fragments in fractures, allowing a good fixation by osteosynthesis.

Cut guides or cutting blocks can be used in an orthopedic surgery to assist a surgeon in cutting or modifying some portions of a target bone. For example, in joint replacement surgeries such as total hip replacement (THR) or total knee replacement (TKR), the preparation of the bones can involve pinning/screwing saw guide cutting blocks to the bones, so that a reciprocating saw blade can be held steady along its intended path. Placement of these blocks can be guided by manual instrumentation or through the use of jigs.

The positioning of cutting blocks can be a time consuming and complicated process, which is critical to positive outcomes for the patient. Mechanisms that allow the cutting blocks to be adjusted within the required workspace are complex, and require high machining tolerances, adding to costs and complexity of these instrument systems.

Manual alignment, in particular, can be cumbersome and is limited to information obtainable through mechanical and visual referencing means. The instruments used to manually align cutting blocks cannot fully capture the 3D shape of the bones, nor can they adequately capture information about kinematics of the joint or soft tissue tension or laxity. Such instruments are expensive to create and to manage. Such instruments require significant operational and cleaning costs. These costs increase the burden of managing cutting blocks. Mechanical referencing instruments can add to the burden of managing cut guides or cutting blocks.

SUMMARY

There is provided a system for drilling holes in a target bone. The system includes a cutting tool, a navigation system configured to track a position of the cutting tool, and a computer-assisted surgical (CAS) system operably connected to the cutting tool and the navigation system. The CAS system configured to determine an implant component to be implanted on the target bone, determine a cutting block position for preparing the target bone to receive the implant component, determine a plurality of pin locations for securing a cutting block to the target bone based upon the determined cutting block position, and selectively provide instructions to the cutting tool to cut a hole when the cutting tool is in a position adjacent to at least one of the determined plurality of pin locations.

In some embodiments, the navigation system may be configured to track the position information for the cutting tool and transmit the position information to the CAS system. In some additional embodiments, the CAS system may be further configured to receive the position information from the navigation system, determine a location and orientation of the cutting tool based upon the received position information, and provide the instructions to cut at least a portion of the hole when the determined location of the cutting tool is adjacent to at least one of the determined plurality of pin locations.

In some embodiments, the CAS system may be further configured to determine implant configuration information, wherein the implant configuration information comprises at least one of hole trajectory information, implant sizing information, labelling information, planar cut positioning information, planar cut orientation information, and associated cutting block information. In some additional embodiments, the CAS system may be further configured to select the cutting block, wherein the cutting block comprises a size and shape, determine hole location information for the selected cutting block based upon the implant configuration information and the cutting block size and shape, and determine the plurality of pin locations based upon the determined hole location information.

In some embodiments, the CAS system may be further configured to receive a surgical plan that defines an implant procedure for the target bone and determine the implant component based upon the received surgical plan. In some additional embodiments, the surgical plan may define a knee replacement procedure.

In some embodiments, the cutting tool is a computer-controlled cutting tool.

In some embodiments, the cutting tool is a handheld cutting tool.

In some embodiments, the cutting block includes an opening configured to constrain a sawblade.

There is also provided a device for assisting in drilling holes in a target bone. The device includes a processing device operably connected to a computer readable medium configured to store one or more instructions. When executed, the instructions cause the processing device to determine an implant component to be implanted on the target bone, determine a cutting block position for preparing the target bone to receive the implant component, determine a plurality of pin locations for securing a cutting block to the target bone based upon the determined cutting block position; and selectively provide instructions to a cutting tool operably connected to the processing device to cut a hole when the cutting tool is in a position adjacent to at least one of the determined plurality of pin locations.

In some embodiments, the one or more instructions may include additional instructions that, when executed, cause the processing device to receive position information for the cutting tool, determine a location and orientation of the cutting tool based upon the received position information, and provide the instructions to cut at least a portion of the hole when the determined location of the cutting tool is adjacent to at least one of the determined plurality of pin locations.

In some embodiments, the one or more instructions may include additional instructions that, when executed, cause the processing device to determine implant configuration information, wherein the implant configuration information comprises at least one of hole trajectory information, implant sizing information, labelling information, planar cut positioning information, planar cut orientation information, and associated cutting block information. In some additional embodiments, the one or more instructions may include additional instructions that, when executed, cause the processing device to: select the cutting block, wherein the cutting block comprises a size and shape; determine hole location information for the selected cutting block based upon the implant configuration information and the cutting block size and shape; and determine the plurality of pin locations based upon the determined hole location information.

In some embodiments, the one or more instructions may include additional instructions that, when executed, cause the processing device to receive a surgical plan that defines an implant procedure for the target bone, and determine the implant component based upon the received surgical plan. In some additional embodiments, the surgical plan may define a knee replacement procedure.

The example embodiments as described above can provide various advantages over prior techniques. For example, the techniques as taught herein can reduce the time spent finding the optimal position for a cutting block for a specific implant component. The techniques also provide for more accurately locating the implant component in the optimal position by utilizing a robotically-assisted surgical system to drill holes in a precise location for pinning the cutting block in the optimal position for a specific implant component.

Further features and advantages of at least some of the embodiments of the present disclosure, as well as the structure and operation of various embodiments of the present disclosure, are described in detail below with reference to the accompanying drawings.

BRIEF DESCRIPTION OF THE DRAWINGS

The accompanying drawings, which are incorporated in and form a part of the specification, illustrate the embodiments of the invention and together with the written description serve to explain the principles, characteristics, and features of the invention. In the drawings.

DETAILED DESCRIPTION

Figure 1:
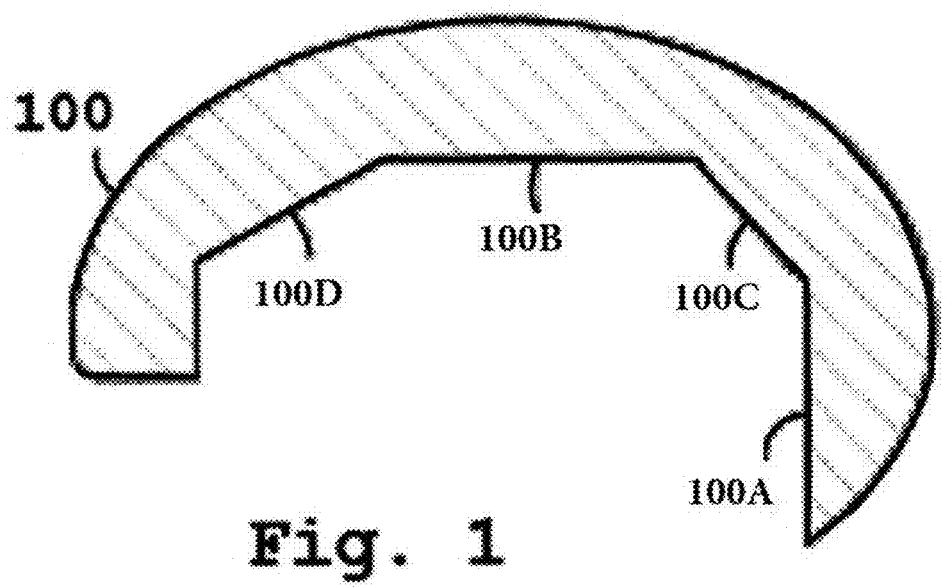
FIG. 1 illustrates an example of an implant that can be attached to a bone as part of a surgical procedure in accordance with certain embodiments of the present disclosure.

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

The embodiments of the present teachings described below are not intended to be exhaustive or to limit the teachings to the precise forms disclosed in the following detailed description. Rather, the embodiments are chosen and described so that others skilled in the art may appreciate and understand the principles and practices of the present teachings.

This disclosure describes example systems and methods of implementing a navigation system to control a drilling device to drill pilot holes in a bone to prepare the bone for attachment to an implant. In the following description, for purposes of explanation, numerous specific details are set forth in order to provide a thorough understanding of example embodiments. It will be evident to one skilled in the art, however, that embodiments can be practiced without these specific details.

For the purposes of this specification, the term "implant" is used to refer to a prosthetic device or structure manufactured to replace or enhance a biological structure. For example, in a knee replacement procedure, an implant can be placed on one or both of the tibia and femur. While the term "implant" is generally considered to denote a man-made structure (as contrasted with a transplant), for the purposes of this specification, an implant can include a biological tissue or material transplanted to replace or enhance a biological structure.

The disclosed navigation system can track a drilling device to determine updated position information for the drilling device. As used herein, position information can include some combination of position information, orientation information, alignment information, and other related spatial information that can be used to determine the current position of the drilling device. The position information can be used to align and/or guide the drilling device to drill the pilot holes in predetermined positions. The system ensures proper placement of a cut guide or cutting block on the bone without the use of jigs or other similar devices that are used to locate the pilot holes in manual procedures or conventional computer-assisted implant surgery. The cut guide or cutting block can be utilized to ensure that the bone, as shaped by the cutting tool, can receive the implant.

The navigation system can be configured to implement a hand-held robotically-assisted tool called the NAVIO®. NAVIO is a registered trademark of BLUE BELT TECHNOLOGIES, INC. of Pittsburgh, PA The navigation system can facilitate the implementation of cutting tools through the NAVIO®. These cutting tools can be tracked to control the cutting action of the cutting element based on its position relative to the bone and the surgical plan.

The navigation system can correlate a planned implant location relative to the bone with a database that contains the necessary pin trajectories associated with each cutting block. The system can utilize the surgical plan and coordinate transforms to define where the cut block design aligns with the necessary cuts for the implant. The system can determine where the pin trajectories lie within in the cut block, which can be used to determine the proper placement of the pilot holes without the need for manual alignment. The system can precisely align the cutting block without the need to utilize a jig that is placed with trackers or couplers to eliminate an unnecessary step in conventional robot-assisted implant surgical procedures.

The disclosed navigation system utilizes direct guidance to drill/mill the pin holes. Then, the cutting blocks are mounted directly on the bone using a pin. This avoids many of the drawbacks associated with the existing methods of robotic-assisted total knee arthroplasty (TKA) in which a robotic hand-piece that includes bur/mill fixation features is used to position the cutting blocks on the bone surface.

It should be noted that, as used herein, using a pin to secure or mount, for example, a cutting block includes using any type of medical fastener such as a pin, post, threaded screw, self-tapping screw, or other similar fastener for mounting the cutting block to a target bone or another similar surface. Similarly, a hole drilled into a target bone can be sized to accommodate some portion of the pin. For example, the hole may be shallowly drilled into the bone for receiving a small portion (e.g., 10% of the length) of the pin for location purposes. Additionally, the hole may be drilled deeply into the bone (e.g., 90% of the length) of the pin for both location and orientation/alignment purposes. In some examples, the depth of the hole may be about 2 cm. In other examples, the depth of the hole may range from about 1.0 cm to about 3.0 cm. In other examples, the depth of the hole may range from about 0.25 cm to about 5.0 cm.

Unlike conventional surgical navigation systems which utilize preoperative imaging, the disclosed navigation system uses imageless registration and planning to drill holes to precisely mount a cutting block to further shape the bone with more efficient instruments (i.e. saws). This feature distinguishes the disclosed navigation system from surgical navigation systems that are used for pedicle screw placement. In such systems, the pedicle screws are the implants.

FIG. 1 illustrates an exemplary implant 100 that can be used in knee replacement surgery. In certain embodiments, the exemplary implant 100 is placed at the distal end of the patient's femur. The implant 100 may be attached to a surface formed from a bone cut on a post-operative bone (not shown). The implant 100 may include an interfacing surface sized and shaped to be in close contact with the post-operative surfaces of the target bone. The interfacing surface may include multiple facets 110A-D oriented in conformity with the cutting planes 110A-D, respectively.

When a surgeon places the implant 100 in a joint, the surgeon must often create holes or channels in the bone that mirror protrusions on the implant 100 that keep it affixed to the bone in the proper position. For optimal fit, the surgeon can use a cutting tool, such as a spinning bur or a saw, to shape the bones to receive corresponding implants with as little gap as possible. Certain embodiments of the invention utilize a sagittal reciprocating saw.

Figure 2A:
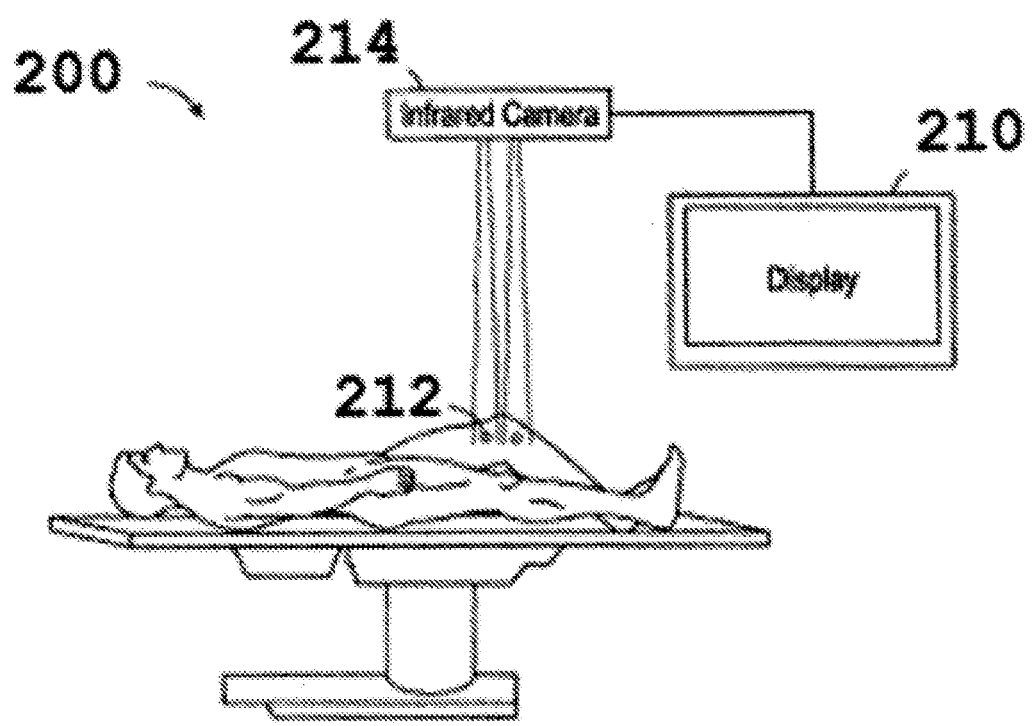
FIG. 2A is a block diagram depicting a system for providing surgical navigation to ensure an orthopedic procedure is consistent with a surgical plan in accordance with certain embodiments of the present disclosure.
Figure 2B:
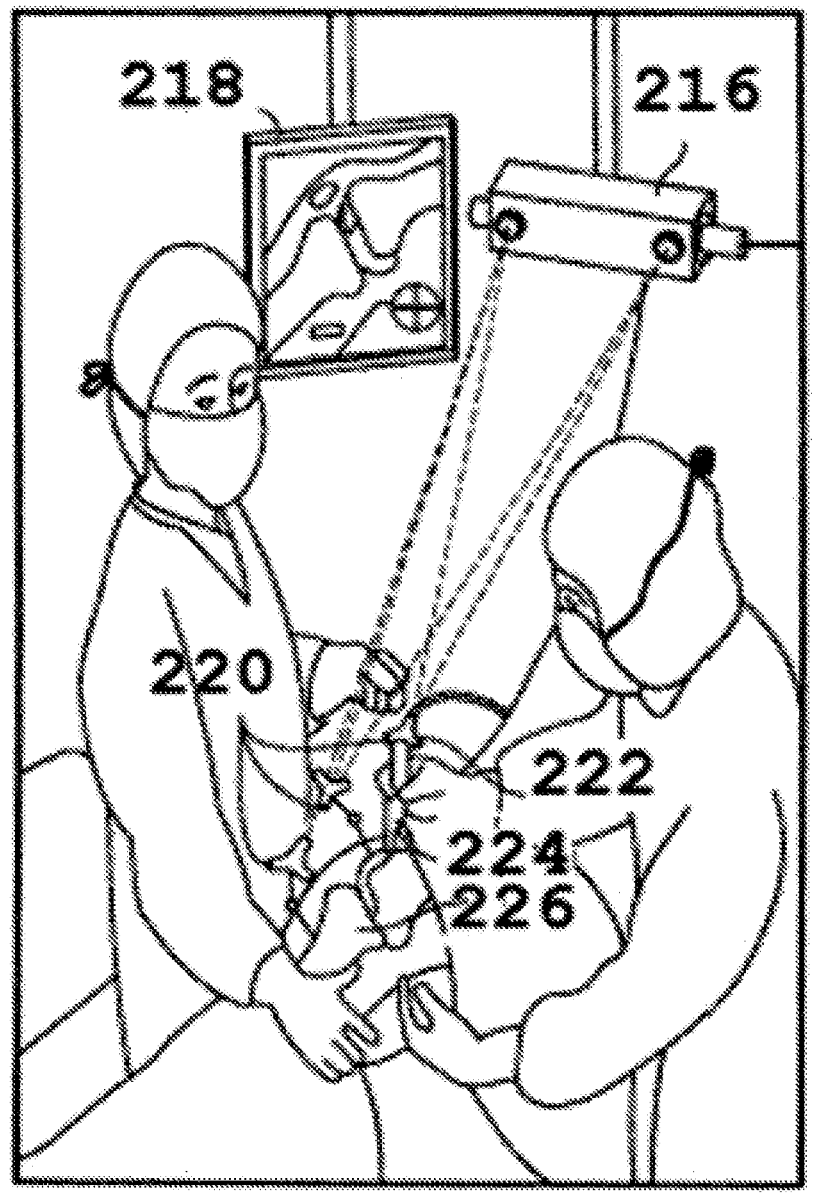
FIG. 2B is an illustration of an operating room with a system employing a cutting tool in accordance with certain embodiments of the present disclosure.
Figure 2C:
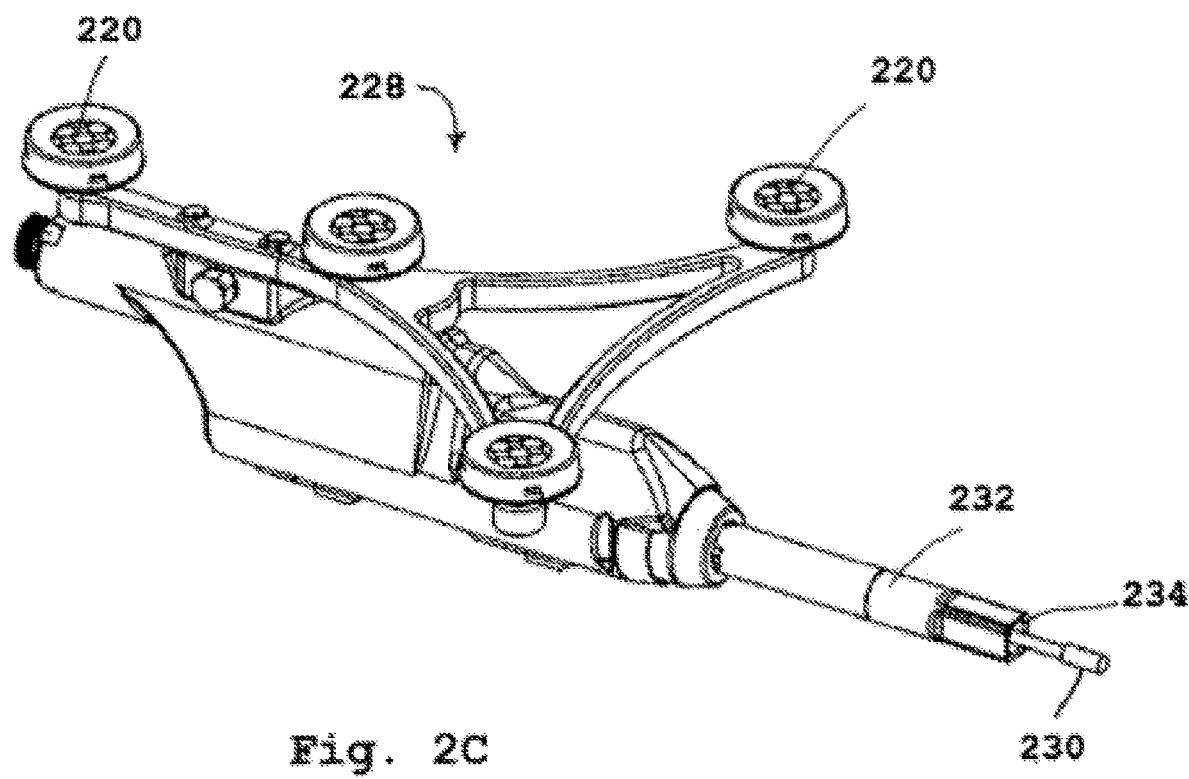
FIG. 2C is a perspective view of a hand-held cutting device with a cut guard in accordance with certain embodiments of the present disclosure.

FIGS. 2A-2C illustrate components of a surgical navigation system 200 for controlling cutting elements during a procedure through virtual placement of an implant, according to certain embodiments. The surgical navigation system 200 may assist a surgeon in cutting or modifying some portions of a target bone. For example, in joint replacement surgeries such as total knee replacement, the surgical navigation system 200 may be used to align and/or to guide the surgeon to selectively cut portions of the ends of the target bones and replace those portions with endoprosthetic implants, such as the implant 100 shown in FIG. 1.

FIG. 2A illustrates a block diagram for the surgical navigation system 200, which includes a computer system 210 to provide a display for viewing location data provided by optical trackers 212 as read by an infrared camera system 214. The optical trackers 212 and infrared camera system 214 may provide data relevant to the precise location of the bones in the knee joint. In certain embodiments, the infrared camera system 214 may detect tracking spheres located on the optical trackers 212 in order to gather location data regarding the patient's femur and tibia on which a procedure is to be performed.

FIG. 2B illustrates an exemplary optical surgical navigation setup. The infrared camera 216 and optical trackers 220 may be used to perform surgical navigation as discussed. The optical trackers 220 may be rigidly attached to any object (such as the surgical tool 226) that the surgeon wishes to track during the procedure. The camera 216 may continuously monitor the workspace during the procedure and the trackers 220 are detected from those images. Using the known rigid spatial relationship of the trackers 220 to a surgical tool, the position of a cutting element 224 on the tool 222 in a three-dimensional space may be tracked and continuously output to the display 218. The display 218 may also continuously display the cutting element 224 location relative to the patient's anatomy.

FIG. 2C illustrates a hand-held cutting tool 228 that may be used in conjunction with certain embodiments of the present invention. As previously disclosed in U.S. Pat. No. 6,757,582 to Brisson et at., the entirety of which is incorporated herein as if more fully set forth, the tool 228 is tracked by a camera (such as camera 216 in FIG. 2B) that optically detects the trackers 220 and communicates that information to a computer system that is also tracking the bones within the surgical space and comparing the location of the tool 228 with a pre-determined surgical plan. In certain embodiments, the tool 228 turns on when the cutting element 230 is in a position where the surgical plan indicates the bone should be cut and then turns off when the tool 228 is near bone that is to be preserved. In certain other embodiments, the cutting element 230 is caused to extend and cut in places where it is supposed to cut and retracts behind the cut guard 232 when it is not supposed to cut the bone. In still further embodiments, the cutting element 230 may be extended a controlled distance away from the guard so that it only cuts to a certain depth or at a certain distance away from the distal end 234 of the guard in accordance with the surgical plan.

Figure 3:
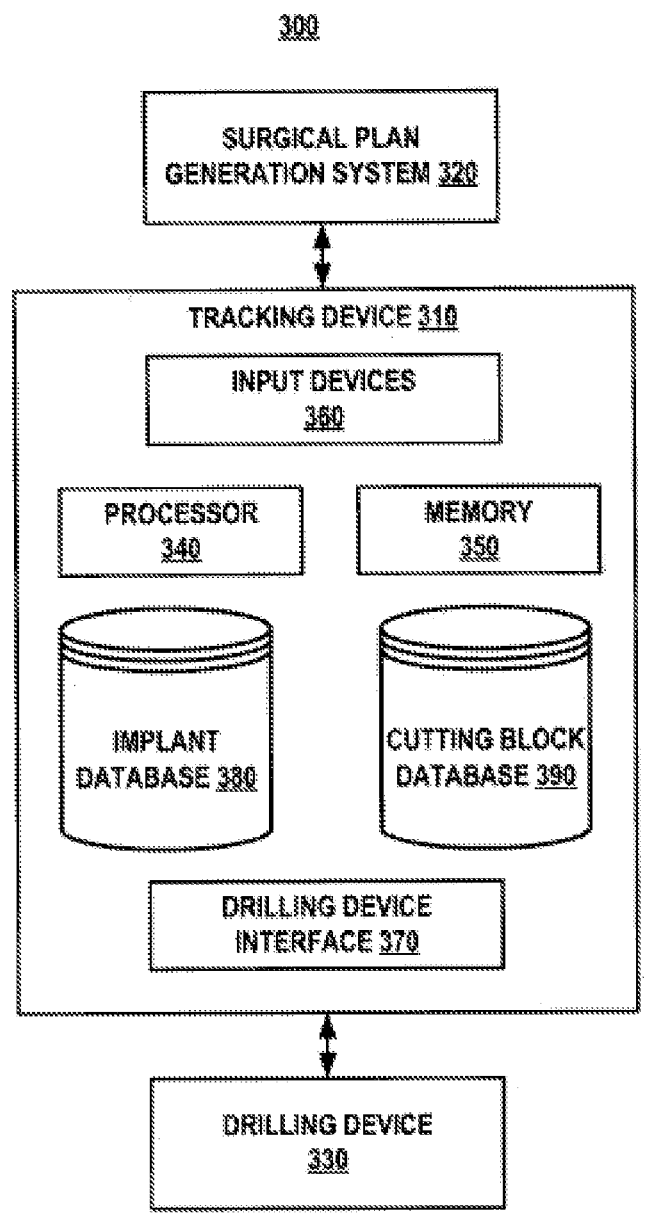
FIG. 3 is a block diagram depicting a system for tracking a drilling device to place one or more pin holes for an implant cutting block pin or pins in accordance with certain embodiments of the present disclosure.

FIG. 3 is a block diagram of an exemplary surgical navigation system 300 that may be configured and implemented to have the functionality to position a cutting element to create pin holes that will properly place cut guides or cutting blocks (not shown) in an appropriate position that is consistent with a pre-determined surgical plan. The surgical navigation system 300 may utilize more information than traditional systems that utilize manually-placed mechanical jigs. The information may include range of motion capture, and intraoperatively or preoperatively defined anatomic landmarks.

The cut guide or cutting block can be attached to the bone to ensure that the cutting tool shapes the bone correctly. The cutting block can be attached to a bone with pins. The cut guide or cutting blocks ensure that the surgeon does not remove too much bone, which may result in an implant that does not fit properly, is loose, or may be subject to implant dislocation or failure.

The surgical navigation system 300 may configure and implement a tracking device 310 that is connected to a surgical plan generation system 320 and a drilling device 330. The surgical navigation system 300 may be configured and implemented as a single system for the alignment of multiple types of jigs to support multiple surgeries and implant designs. It is to be appreciated that embodiments of the described subject matter may be implemented by various types of operating environments, computer networks, platforms, frameworks, computer architectures, and/or computing devices.

The tracking device 310 may align and/or control the drilling device 330 to drill pin holes in a bone in accordance with a surgical plan that is generated by the surgical plan generation system 320. The pin holes are aligned for proper placement of a cut guide or cutting block (not shown) on the bone by the navigation system 300 and the tracking device 310. In certain embodiments, the drilling device 330 may be controlled by a robot that is programed to drill the pin holes. In certain other embodiments, the drill may be tracked by the navigation system and manually operated by a member of the surgical team.

The tracking device 310 and/or the surgical plan generation system 320 may include one or more processors and memory devices, as well as various input devices, output devices, communication interfaces, and/or other types of devices. The tracking device 310 and/or the surgical plan generation system 320 may include a combination of hardware and software.

The tracking device 310 and/or the surgical plan generation system 320 may implement and utilize one or more program modules or similar sets of instructions contained in a computer readable medium or memory (e.g., memory 350) for causing a processing device (e.g., processor 340) to perform one or more operations. Generally, program modules include routines, programs, objects, components, data structures, etc., that perform particular tasks or implement particular abstract data types.

The tracking device 310 and/or the surgical plan generation system 320 may be implemented by one or more computing devices such as computers, PCs, server computers configured to provide various types of services and/or data stores in accordance with aspects of the described subject matter. Exemplary server computers may include, without limitation: web servers, front end servers, application servers, database servers, domain controllers, domain name servers, directory servers, and/or other suitable computers. Components of tracking device 310 and/or surgical plan generation system 320 may be implemented by software, hardware, firmware or a combination thereof.

The tracking device 310 may include the processor 340, memory 350, input devices 360, drilling device interface 370, implant database 380, and cutting block database 390. The input devices 360 may be configured and implemented to receive a surgical plan from the surgical plan generation system 320 for attaching an implant to a bone. The surgical plan may utilize a cutting block to guide a cutting tool to remove a portion of the bone to facilitate accurate placement of the implant. The surgical plan may be utilized by the processor 340, immediately, or may be stored in memory 350 for later use. It should be understood that the tracking device 310 may configure and implement a single database that may be partitioned into the implant database 380 and the cutting block database 390.

The tracking device 310 may configure and implement the processor 340 to access the implant database 380 to identify the implant (or implants) that are the subject of the surgical plan. The processor 340 may obtain implant geometry for the implant(s) from the implant database 380. The processor 340 may determine the implant location relative to the bone from the surgical plan.

The tracking device 310 may configure and implement the processor 340 to access the cutting block database 390. The processor 340 may utilize the cutting block database 390 to determine the cutting block position relative to the implant location for the surgical plan. The processor 340 may obtain at least one cutting tool trajectory from the cutting block database 390.

Once the processor 340 obtains the above-described information for the implant and the cutting block, the processor 340 may determine on or more pin locations (usually a pair) for attaching the cutting block to the bone. The processor 340 may utilize the relationship between the implant location, the cutting block position, and the cutting tool trajectory to determine the pin locations.

The tracking device 310 may configure and implement the drilling device interface 370 to track the drilling device 330 to position the drilling device 330 over one of the pin locations. The drilling device 330 may drill a hole at the pin location. Then, the drilling device interface 370 may align the drilling device 330 to position the drilling device 330 over a second pin location. The drilling device 330 may drill a hole at the second pin location.

The drilling device 330 may include any type of tracked tool, robotic hand-piece, or autonomous robot that facilitates the ability to drill holes according to the necessary position and orientation guided or governed by the tracking device 310. It should be also noted that the drilling device 330 is described herein by way of example only. In certain implementations, additional cutting tools can be used to create the holes at the pin locations. For example, a saw including a moving or reciprocating saw blade can be used to create the holes and the pin locations.

The implant database 380 may include information for each implant and/or implant design family (e.g. Journey II, Legion, Genesis), including information for each size component. The information may include the 3D shape of the implant (e.g. STL data), mounting implant peg hole trajectories (defined in the coordinate space of the 3D shape data), metadata describing sizing and labelling information, and geometry information describing the position and orientation of planar cuts to be made with a saw in order to install the implant. Each implant in the implant database 380 may be correlated with one or more compatible cut guide or cutting block.

The cutting block database 390 includes information relating one or more cut guide or cutting block to compatible implants in the implant database 380. The cutting block database 390 may physically define saw cut trajectories relative to a particular cut guide or cutting block. The cut guide or cutting blocks may be pinned to the bone to hold them rigidly to the bone during the cut. The cutting block database 390 may include information relating to pin holes for a particular cut guide or cutting block.

The cutting block database 390 may contain trajectory and placement data relating to the pin holes for each cut guide or cutting block. The cutting block database 390 may contain coordinate transform information (either explicitly, through specification in the cutting block database 390, or implicitly through assumed common coordinate definitions). The coordinate transforms may describe an expected alignment for the cut guide or cutting block, as well as implant coordinate systems. The implant coordinate systems may indicate how cut trajectories may coincide with the necessary planar cuts for installation of the implant.

The tracking device 310 may configure and implement the processor 340 to correlate a planned implant location relative to the bone utilizing the information contained in the implant database 380 and the cutting block database 390. The processor 340 may utilize surgical navigation principles to determine the proper pin placement when three variables are known. The variables include the location of the implant (relative to the tracker), the proper placement of the cut guide (or cutting block) to align the expected cuts with the implant shape, and the location of the pins are for a particular cut guide (or cutting block).

The processor 340 may utilize the surgical plan and the coordinate transforms to determine a necessary pin placement through the equation:

trackerTpin=trackerTimplant*implantTcutblock*cutblockTpin where trackerTpin represents at least one of the pin locations, trackerTimplant represents the position of the implant on the bone, implantTcutblock represents the position of the cutting block on the bone, and cutblockTpin represents the cutting tool trajectory.

The processor 340 may utilize other surgical navigation principles and coordinate transforms. For example, the processor 340 may utilize coordinate transforms for implants that include parallel facets that allow for sliding along a common direction (e.g., for a total knee implant, mediolaterally). Such transforms include a degree of freedom that gives flexibility to a cut guide or cutting block that may be relative to a planned location for an implant. In such transforms, the ImplantTcutblock variable may be initialized to a nominal position, such that the processor 340 may allow for further manipulation along this degree of freedom.

Figure 4A:
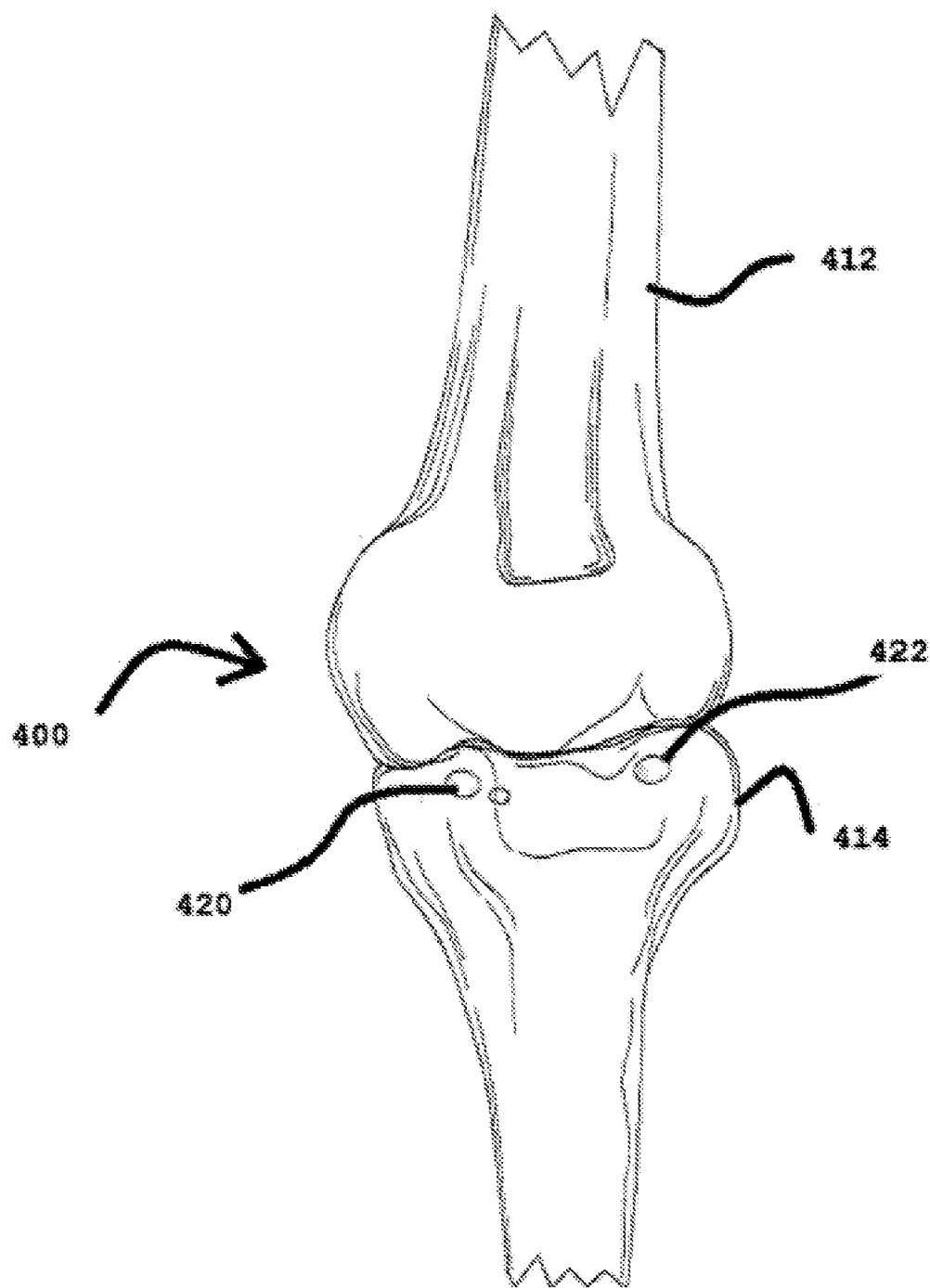
FIG. 4A is a perspective view of a knee joint showing a femur, a tibia, and a pair of pin holes in accordance with certain embodiments of the present disclosure.
Figure 4B:
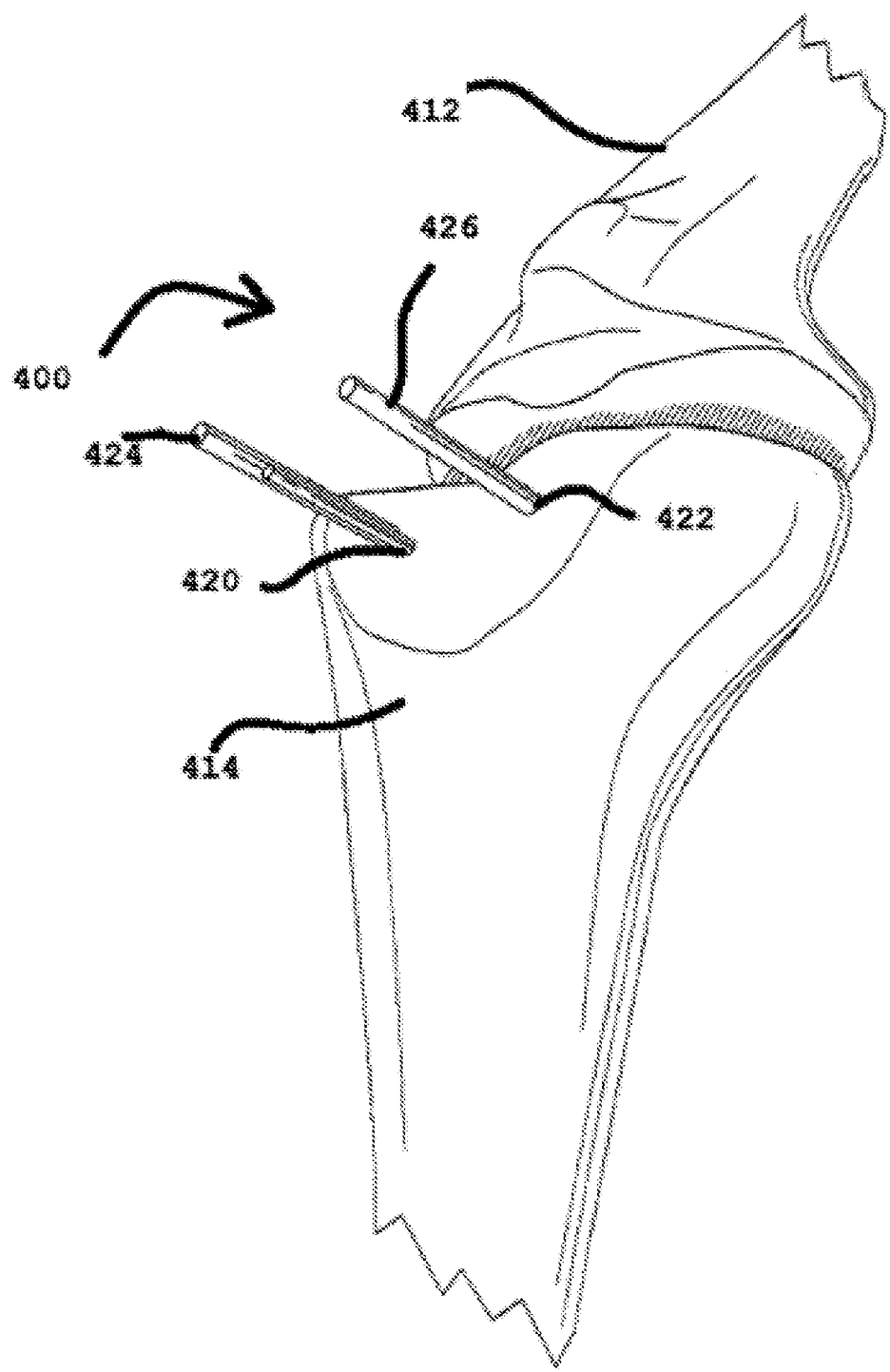
FIG. 4B is a perspective view of a knee joint showing a femur, a tibia, and a pair of pins that have been placed in the pin holes shown in FIG. 4A in accordance with certain embodiments of the present disclosure.
Figure 4C:
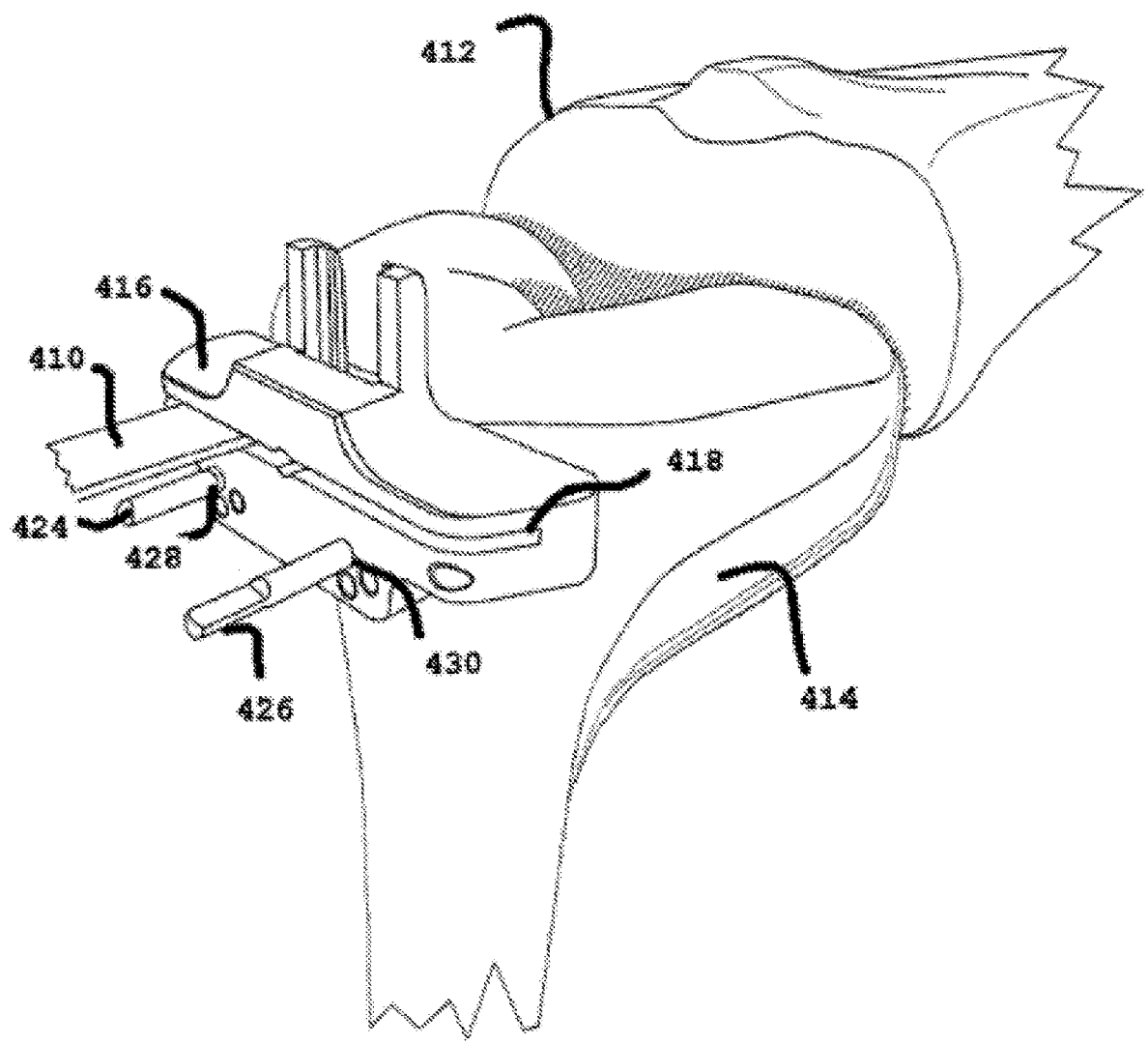
FIG. 4C is a perspective view of a knee joint showing a femur, a tibia, a pair of pins, and a cutting block in accordance with certain embodiments of the present disclosure.

FIGS. 4A-4C illustrate an example of a knee joint 400 that is being prepared for shaping by a cutting tool 410 to form one or more surfaces for receiving an implant, such as implant 100 shown in FIG. 1. The knee joint 400 includes a femur 412 and a tibia 414. A cutting block 416 is positioned on the tibia 414 to ensure that the cutting tool 410 makes the proper cut on the tibia 414 without removing an excess amount of bone material. The cutting block 416 may be aligned on the tibia 414 without having to use manual instrumentation sets, so that the cutting block 416 may be smaller and less intricate than conventional cut guides, cutting blocks, and/or jigs.

The cutting block 416 includes a channel or slot 418 to guide the cutting tool 410. The slot 418 constrains the cutting tool 410 to eliminate vibration and errant cuts during cutting operations. For example, the slot 418 can be configured to restrain a saw blade of the cutting tool 410. In this exemplary embodiment, the slot 418 should be parallel to a bone removal line on the tibia 414.

FIG. 4A illustrates the femur 412 in an essentially vertical alignment with the tibia 414. The tibia 414 includes a pair of pin holes 420 and 422 that have been produced with a drilling device, such as the drilling device 330, shown in FIG. 3. In this exemplary embodiment, the positions of the pin holes 420 and 422 have been determined by the processor 340 using information contained within the implant database 380 and the cutting block database 390. The tracking device 310 utilized the drilling device interface 370 to make sure that the drilling device 330 positioned the pin holes 420 and 422 in the proper positions.

FIG. 4B illustrates the femur 412 tilted at a slight angle with respect to the tibia 414. A first pin 424 has been inserted into pin hole 420. A second pin 426 has been inserted into pin hole 422. The pins 424 and 426 are oriented in a manner to support the cutting block 416 on the tibia 414 in an orientation that will allow the tibia 414 to be shaped to support an implant, such as the implant 110 shown in FIG. 1.

FIG. 4C illustrates the cutting block 416 being attached to the tibia 414. The tibia 414 is abuts the femur 412 with the femur 412 being aligned essentially perpendicularly to the tibia 414. The cutting block 416 includes a pair of pin holes 428 and 430 for receiving the pins 424 and 426.

It should be noted that attaching a cutting block to a tibia as shown in FIGS. 4A-4C is provided by way of example only. In certain implementations, the processes and techniques as described herein can be used to prepare holes in additional bones for mounting of a cutting block thereon. For example, holes may be prepared in a femur for attachment of a cutting block to prepare the femur to receive a femoral implant component. Similarly, holes may be prepared in a vertebra for receiving a cutting block for preparing at least a portion of a patient's spine for receiving an interbody spinal implant.

Figure 5:
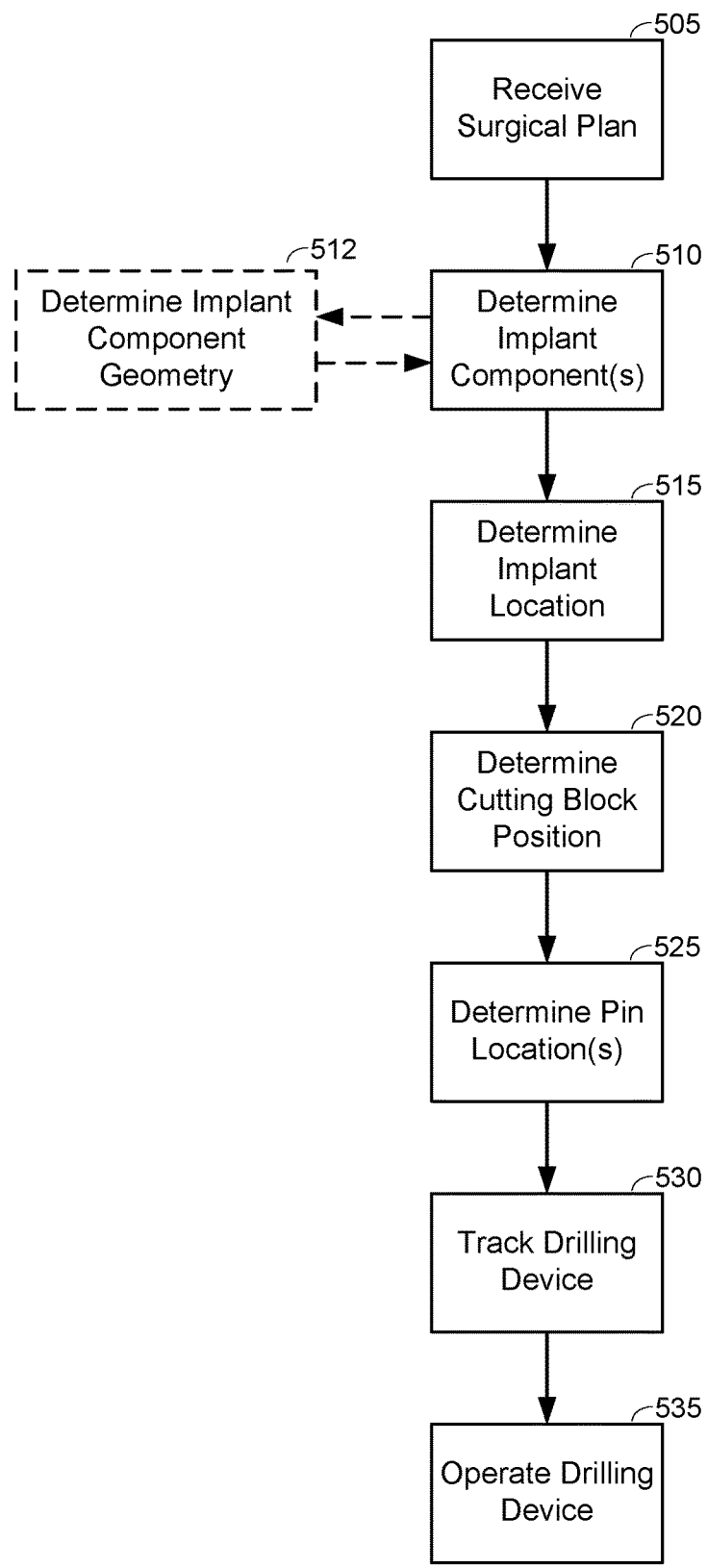
FIG. 5 is a flow diagram showing a sample process for positioning a cutting block in accordance with certain embodiments of the present disclosure.

FIG. 5 illustrates a sample process for using a computer-assisted surgical (CAS) system, such as the surgical systems described above, for drilling hole in a target bone for mounting, for example, a cutting block. The CAS system may receive 505 a surgical plan including, for example, information related to the surgical procedure such as surgery type (e.g., total knee replacement, partial knee replacement), implant family, implant size, optimal implant location, and other related information. Based upon the surgical plan, the CAS system may determine 510 the implant component that is to be used during the procedure. In some examples, the CAS system may determine 510 the implant component by extracting this information from the surgical plan. In other examples, the CAS system may determine 510 the implant component based upon a selection of the implant component by, for example, a surgeon performing the procedure. In some examples, the CAS system may optionally determine 512 implant component geometry based upon the determine

510 implant component. For example, as noted above, the CAS system may access a database or other similar data store to determine 512 the implant component geometry.

The CAS system may also determine 515 the implant location for the patient. In some examples, the surgeon may use a display device or other similar device operably connected to the CAS system to change or otherwise adjust the location of the implant. Based upon the implant position, the CAS system may determine 520 the cutting block location. In some implementations, determining 520 the cutting block location may include selecting the cutting block to use and determining the size and shape of the cutting block.

The CAS system may also determine 525 the pin locations for the cutting block based upon the cutting block location and, based upon the pin locations, the pin hole locations on the target bone. In some implementations, determining 525 the pin and hole locations may be based upon the size and shape of the cutting block. For example, depending upon the size of cutting block, the CAS system may determine two or three pin and hole locations. For example, the cutting block may include two surface pins for mounting the cutting block to a target bone, and a third hole positioned such that a third pin is placed at an angle to the first two pins, thereby locking the cutting block into position on the bone. In such an example, the CAS system may determine three pin and associated pin hole locations.

The CAS system may also track 530 the drilling device using, for example, location information received from a navigation system as described above. For example, the navigation system may be configured to record and transmit position information related to the current position of the cutting tool to the CAS system. The CAS system can receive this information, and determine location and orientation information for the cutting tool based upon the position information. Depending upon the current position of the cutting device, the CAS system may operate 535 the drilling device by selectively providing operation instruction to the cutting device. For example, the CAS system determines that the drilling device is in a position adjacent to one of the pin hole locations, the CAS system may provide instructions for the cutting tool to align with the hole location and drill at least a portion of the hole. In certain implementations, the drilling device may include a drill bit, or other cutting device, that includes an adjustable alignment for fine aiming of the drilled hole. In such an example, the CAS system can provide instructions for the drilling device to align the drill bit with the hole to be drilled and drill the whole as appropriate.

It should be noted that the process as shown in FIG. 5 is provided by way of example only. In certain implementation, the process steps shown, and the order performed, can be altered accordingly. For example, the CAS system may be configured to continually track 530 the drilling device throughout the surgical procedure, and not merely limited to tracking the surgical device as shown in the process order of FIG. 5 and described in the above discussion, In some implementations, there is also provided a method for drilling holes in a target bone. The method includes receiving an indication of an implant component to be implanted on the target bone, determining a cutting block position for preparing the target bone to receive the implant component, determining a plurality of pin locations for securing a cutting block to the target bone based upon the determined cutting block position, and selectively providing instructions to a cutting tool operably connected to the processing device to cut a hole when the cutting tool is in a position adjacent to at least one of the determined plurality of pin locations.

In some embodiments, providing instructions to the cutting tool may include receiving position information for the cutting tool, determining a location and orientation of the cutting tool based upon the received position and orientation information, and providing the instructions to cut at least a portion of the hole when the determined location of the cutting tool is adjacent to at least one of the determined plurality of pin locations.

In some embodiments, the method may include determining implant configuration information, wherein the implant configuration information comprises at least one of hole trajectory information, implant sizing information, labelling information, planar cut positioning information, planar cut orientation information, and associated cutting block information.

In some additional embodiments, determining the cutting block position may include: selecting the cutting block, wherein the cutting block comprises a size and shape; determining hole location information for the cutting block based upon the implant configuration information and the cutting block size and shape; and determining, by the processing device, the plurality of pin locations based upon the determined hole location information.

In some embodiments, receiving an indication of the implant component may include receiving a surgical plan that defines an implant procedure for the target bone and selecting the implant component based upon the received surgical plan.

In some additional embodiments, the surgical plan may define a knee replacement procedure.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A system for preparing a target bone for receiving a cutting block, the system comprising:
    a computer-assisted surgical (CAS) system configured to:
        determine an implant component to be implanted on the target bone,
        determine a cutting block position for the cutting block configured for preparing the target bone to receive the implant component,
        align the cutting block to the target bone based on the determined cutting block position based on alignment of a first cutting plane corresponding to the implant component and a second cutting plane corresponding to the cutting block,
        determine a tool trajectory for a surgical tool according to the determined cutting block position, and
        control the surgical tool according to the determined tool trajectory to cause the surgical tool to prepare the target bone for placement of the cutting block.

2. The system of claim 1, wherein the CAS system is further configured to:
    receive a surgical plan that defines an implant procedure for the target bone; and
    determine the implant component based upon the received surgical plan.

3. The system of claim 2, wherein the surgical plan defines a knee replacement procedure.

4. The system of claim 1, wherein the second cutting plane corresponds to an opening on the cutting block, the opening configured to constrain a sawblade.

5. The system of claim 1, further comprising:
    a tracking system coupled to the CAS system, the tracking system configured to track one or more trackers disposed on the surgical tool;
    wherein the CAS system is configured to determine the tool trajectory via the tracking system.

6. The system of claim 5, wherein the one or more trackers comprise optical trackers.

7. The system of claim 1, wherein the CAS system is further configured to:
selectthe cutting block from a plurality of cutting blocks, wherein the selected cutting block corresponds to the implant component.

8. A system for preparing a target bone for receiving a cutting block, the system comprising:
a computer system comprising a processor and a memory, the memory storing instructions that, when executed by the processor, cause the computer system to:
determine an implant component to be implanted on the target bone,
determine a cutting block position for the cutting block configured for preparing the target bone to receive the implant component,
align the cutting block to the target bone based on the determined cutting block position based on alignment of a first cutting plane corresponding to the implant component and a second cutting plane corresponding to the cutting block,
determine a tool trajectory for a surgical tool according to the determined cutting block position, and
control the surgical tool according to the determined tool trajectory to cause the surgical tool to prepare the target bone for placement of the cutting block.

9. The system of claim 8, wherein the memory stores further instructions that, when executed by the processor, cause the computer system to:
receive a surgical plan that defines an implant procedure for the target bone; and
determine the implant component based upon the received surgical plan.

10. The system of claim 9, wherein the surgical plan defines a knee replacement procedure.

11. The system of claim 8, wherein the second cutting plane corresponds to an opening on the cutting block, the opening configured to constrain a sawblade.

12. The system of claim 8, further comprising:
a tracking system coupled to the computer system, the tracking system configured to track one or more trackers disposed on the surgical tool;
wherein the memory stores further instructions that, when executed by the processor, cause the computer system to determine the tool trajectory via the tracking system.

13. The system of claim 12, wherein the one or more trackers comprise optical trackers.

14. The system of claim 8, wherein the computer system is further configured to:
select the cutting block from a plurality of cutting blocks, wherein the selected cutting block corresponds to the implant component.

* * * * *